United States Patent [19]

Holmes

[11] Patent Number: 5,180,665
[45] Date of Patent: Jan. 19, 1993

[54] METHOD FOR QUANTITATIVELY ASSAYING THE PRESENCE OF DIARRHETIC SHELLFISH POISONING TOXINS IN MARINE SAMPLES

[75] Inventor: Charles Holmes, Edmonton, Canada

[73] Assignee: Her Majesty the Queen in right of Canada, as represented by The National Research Council of Canada, Ottawa, Canada

[21] Appl. No.: 615,711

[22] Filed: Nov. 21, 1990

[51] Int. Cl.$^5$ .............................................. C12Q 1/42
[52] U.S. Cl. ...................... 435/21; 435/194; 435/118; 435/119; 435/267; 435/268; 549/343; 530/352; 424/520; 424/547; 436/63; 436/177; 436/178; 436/503
[58] Field of Search .................. 435/194, 118, 119, 21, 435/7.21, 15, 267, 268; 549/343; 530/352; 204/157.15, 299 R, 180.1; 436/15, 177, 503, 178, 504, 87, 35, 63, 57, 804, 161, 173; 210/198.2, 768, 767, 633, 602, 601, 656, 660, 668, 669; 250/282; 423/299, 249; 424/520, 530, 547

[56] References Cited

U.S. PATENT DOCUMENTS

| | | | |
|---|---|---|---|
| 4,302,470 | 11/1981 | Schmitz et al. | 424/283 |
| 4,314,057 | 2/1982 | Schmitz et al. | 424/283 |
| 4,681,842 | 7/1987 | Rosalki | 435/21 |
| 4,710,469 | 12/1987 | Liang et al. | 435/194 |
| 4,970,226 | 11/1990 | Sun et al. | 514/397 |

OTHER PUBLICATIONS

Cohen et al., Trends in Biochem. Sci, 1990, vol. 15(3), pp. 98–102.
Bialojan et al., Biochem. J. (1988), vol. 256, pp. 283–290.
Haystead et al., Nature, (1989), vol. 337, pp. 78–81.
Shiraki et al., Chemical Abstracts, vol. 110(25), Jun. 19, 1989, #226683b.
Shiraki et al., Chemical Abstracts, vol. 105(7), Aug. 18, 1986, #55751n.
Holmes et al., FEBS Letters, vol. 270(1-2), Sep. 1990, pp. 216–218.
Bergmeyer et al., Meth. Enz. Anal., 3rd ed., vol. IV, pp. 120–126 (1984).
Cohen et al., J. Biol. Chem., vol. 264(36), 1989,pp. 21435–21438.
Tachibana et al., J. Am. Chem. Soc., 1981, vol. 103, pp. 2469–2471.
Holmes, Charles F. B., Chemical Abstracts, vol. 114(25), Jun. 24, 1991, #242173y.
Schmitz et al., *J. Am. Chem. Soc.*, 1981, vol. 103, pp. 2467–2469.
Kupchan et al., *J. Org. Chem.*, 1973, vol. 38(1), pp. 177–179.
Fujisawa Pharm. Co., Ltd., *Chemical Abstracts*, 1982, vol. 96(2), #217820j.

*Primary Examiner*—Johnnie R. Brown
*Assistant Examiner*—Pamela S. Webber
*Attorney, Agent, or Firm*—Iver P. Cooper

[57] ABSTRACT

The present invention relates to a method for quantitatively assaying the presence of DSP toxins such as okadaic acid and dinophysistoxin-1 in marine samples. The method comprises the steps of preparing a marine extract, fractionating the prepared marine extract and selecting the extract fraction containing the toxin to be assayed. Once the desired extract fraction has been selected, a labelled substrate for protein phosphatase and at least one protein phosphatase are added to the extract in an assay. The amount of toxin present is quantitatively measured by the ability of the extract fraction to inhibit catalysis, mainly dephosphorylation, of the labelled substrate by protein phosphatases, such as phosphatase-1 (PP1) or phosphatase-2A (PP2A). Preferably, the method of the present invention is used to assay the presence of okadaic acid in marine organisms such as mussels, oysters, scallops, phytoplankton and the like.

17 Claims, 3 Drawing Sheets

METHOD FOR QUANTITATIVELY ASSAYING THE PRESENCE OF DIARRHETIC SHELLFISH POISONING TOXINS IN MARINE SAMPLES

FIELD OF THE INVENTION

The present invention relates to a method for assaying the presence of diarrhetic shellfish poisoning (DSP) toxins such as okadaic acid (OA) and dinophysistoxin-1 (DTX-1) in marine samples. The method is based on assaying the ability of the toxins to potentially and specifically inhibit protein phosphatases, combined with the use of a technique allowing fractionation of the marine sample extract to be assayed.

BACKGROUND OF THE INVENTION

Diarrhetic shellfish poisoning (DSP) is a gastrointestinal illness of varying severity caused by consumption of shellfish contaminated with certain dinoflagellates. It is caused by toxins which are accumulated in the midgut glands of bivalves feeding on dinoflagellates such as Dinophysis sp. and Prorocentrum sp. These types of organisms are part of the marine plankton shellfish ingest through filter feeding. Therefore, since considerable quantities of plankton are absorbed by filtering organisms, the bivalves may potentially accumulate substantial amounts of toxins.

During the period ranging from 1976 to 1982, over 1000 people were treated for gastroenteritis in Japan after having consumed boiled mussels, scallops and clams. Also, numerous cases of DSP have been reported in countries such as Mexico, Spain, The Netherlands, Scandinavia, France and South America. The high morbidity rate and worldwide distribution of DSPs make it a serious threat to both the shellfish industry and to public health.

One of the major components of the toxic profile associated with DSP is okadaic acid, although other polyether toxins such as yessotoxin, dinophysistoxin-3 and pectenotoxin may also be involved. Okadaic acid was first isolated from the marine sponges *Halichondria okadaii* and *Halichondria melanodocia* and reported by Tachibana et al. in 1981, J. Am. Chem. Soc. 103, 2469-2472.

In recent years, okadaic acid and dinophysistoxin-1 have been found to be powerful tumour promoters. In two-stage carcinogenesis experiments on mouse skin, these compounds were found to be of comparable potency to agents like phorbol esters. Because of their tumor promoting properties, currently acceptable quarantine levels for these toxins (200 ng/g shellfish tissue) therefore appear to be much higher than what should actually be tolerated. In fact, there is a strong possibility that, based on future injection studies in animals, shellfish contaminated even with minute amounts of DSP toxins will be declared unsuitable for human consumption. Hence, it would appear desirable to develop an assay which would permit the detection of very low concentrations of DSP toxins.

The analysis of DSP toxins such as okadaic acid and dinophysistoxin-1 presents a formidable challenge due to their low concentrations in complex mixtures and lack of a characteristic chromophore. The non-specific mouse bioassay has routinely been employed for monitoring DSP. However, there is considerable margin of error in its use and it is imprecise in defining a causative toxin in contaminated samples. This was discussed by Yasumoto et al. in 1985, Tetrahedron 41, 1019-1025.

Recently, a sensitive monoclonal antibody based assay, specific for okadaic acid-related DSP's, was developed as an easy to use field kit. This technology is described by Usagawa et al. in 1989, Toxicon 27, 1323-1330. A specific radioimmunoassay was also described by Levine et al in 1988, Toxicon 26, 1123-1128. This assay detects okadaic acid with a reported detection sensitivity of 160 pg. However, okadaic acid can be biologically inactivated by a single methyl esterification and therefore, since these procedures give no information on the viable biological activity of a detected toxin, they still require validation by activity-based methods of analysis.

Physico-chemical techniques have also been successfully employed to analyze ng quantities of okadaic acid and dinophysistoxin-1, either indirectly by pre-column derivatisation with 9-anthryldiazomethane (ADAM) followed by liquid chromatography (LC) or directly by LC-linked ion-spray mass spectrometry.

It was recently found that okadaic acid is a potent and specific inhibitor of protein phosphatase-1 (PP1) and protein phosphatese-2A (PP2A), two of four major protein phosphateses in the cytosol of mammalian cells that dephosphorylate serine and threonine residues. These finding were documented by Bialojan et al. in 1988, Biochemical Journal 256, 283-290; Haystead et al. in 1989, Nature 337, 78-81 and Cohen et al. in 1989, J. Biol. Chem. 264, 21435-21438. However, when crude marine extracts from shellfish or phytoplankton are assayed for okadaic acid using a protein phosphatese, it is difficult to evaluate whether the inhibitory response results from heterogenous or homogenous activity. Hence, since okadaic acid is not the only compound which inhibits the enzymatic activity of protein phosphatases, and this may be especially important in the case of shellfish which are filtering organisms, it is virtually impossible to determine the organisms, presence of okadaic acid simply by analyzing the inhibitory effect of a crude sample on a given protein phosphatase.

Thus, there is still a great need for an efficient marine bioscreen for DSP toxins such as okadaic acid and related derivatives.

SUMMARY OF THE INVENTION

In accordance with the present invention, there is provided a method for quantitatively assaying the presence of DSP toxins such as okadaic acid and dinophysistoxin-1 in marine samples. The method comprises the steps of preparing a marine extract, fractionating the prepared marine extract and selecting the extract fraction containing the toxin to be assayed. Once the desired extract fraction has been selected, a labelled substrate for protein phosphatase and at least one protein phosphatase are added to the extract in an assay. The amount of toxin present is quantitatively measured by the ability of the extract fraction to inhibit catalysis, mainly dephosphorylation, of the labelled substrate by protein phosphatases, such as phosphatase-1 (PP1) or phosphatase-2A (PP2A).

Preferably, the method of the present invention is used to assay the presence of okadaic acid in marine organisms such as mussels, oysters, scallops, phytoplankton and the like.

The problems encountered in currently available methods used to analyze DSP toxins have therefore been circumvented by providing an analytical procedure of unprecedented sensitivity. This combines, for the first time, a specific physiological activity quantitation technique (based on the inhibition of protein phosphatase) with a highly selective separation technique.

The present invention is more readily illustrated by the following description.

IN THE DRAWINGS

DETAILED DESCRIPTION OF THE INVENTION

Figure 1:
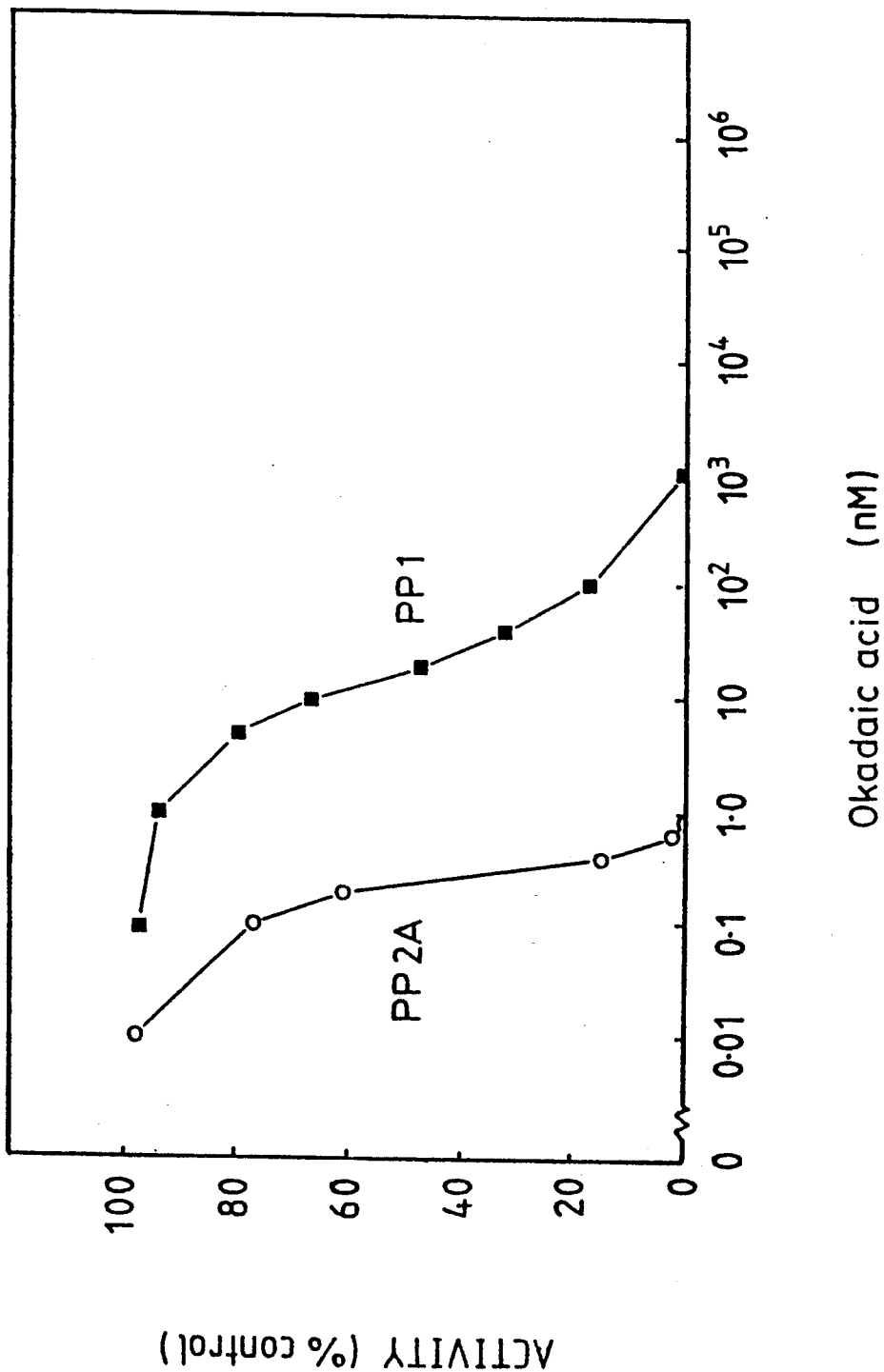
FIG. 1 represents standard curves for the inhibition of protein phosphatase-1 and -2A catalytic subunits by okadaic acid in the phosphorylase a phosphatase assay.

The present invention relates to a process useful in the quantitative analysis of marine samples suspected of containing DSP toxins such as okadaic acid and dinophysistoxin-1. This is achieved by combining (a) a technique for biologically detecting the presence of the toxin through an inhibition assay (using a labelled substrate for protein phosphatase and at least one protein phosphatase, preferably phosphatase-1 and/or -2A), with (b) fractionation techniques, thereby allowing one to assay only the desired toxin.

Exact quantitation of the assayed toxin is achieved by manipulating the concentration of the marine extract fraction such that the degree of inhibition falls within a standard curve defined for inhibition of protein phosphatases with known amounts of toxin.

Up to the present, okadaic acid has generally been viewed as a useful tool in the study of cellular control mechanisms and it has been suggested to routinely include okadaic acid in phosphorylation assays to assist in the detection of protein kinases. Nowhere in the prior art has it been suggested to use protein phosphatases to detect the presence of okadaic acid in marine samples. In other words, okadaic acid has been viewed mainly as a test substance for detecting the presence of protein phosphatases and this property of the acid has been useful in the study of phosphorylation-regulated systems. However, although the inhibitory effect of okadaic acid on protein phosphatases has been known for at least two years, nobody seems to have used protein phosphatases to detect okadaic acid in marine samples.

The separation of a marine sample extract in small fractions constitutes an important aspect of the process of the present invention. An efficient way to fractionate the extract is, for example, to use reverse phase high performance liquid chromatography. The analyzed fractions may then be compared with an okadaic acid standard. Without an appropriate separation technique, it is very difficult to conclude with certainty that the enzymatic activity of the protein phosphatase is inhibited by okadaic acid present in the sample. In fact, the assayed enzyme could, in some instances, be inhibited by another substance, either produced or accumulated by the assayed organism. Hence, the fractionation of the sample is coupled with an appropriate biological detection technique. It allows one to obtain a sensitivity that is about 1000 times higher than the sensitivity achieved with current okadaic acid screening procedures. This enhanced sensitivity appears to open up the possibility of routinely screening phytoplankton for okadaic acid.

General Outline of the Process of the Present Invention

Marine extracts are first homogenized in a solvent which should allow solubilization of all marine toxins present in the sample to be analyzed. Suitable solvents include methanol, acetone and the like.

The marine extracts are then screened for their ability to inhibit protein phosphatase catalytic subunits in a standard assay.

Based on a quantitative standard curve for the toxin to be assayed, samples containing the desired levels of toxin, when assayed against either PP1, PP2A or any related protein phosphatase that is as sensitively and specifically inhibited by the assayed toxin, are fractionated through a suitable fractionation technique. Numerous fractionation techniques may be applied to the process of the present invention. Amongst the most suitable ones, there may be mentioned capillary zone electrophoresis and liquid chromatography, particularly reverse phase liquid chromatography.

Selected fractions are then screened by differential inhibition assay of protein phosphatase, preferably PP1 and/or PP2A. Since the chemical reaction involved with phosphatase action is a phosphate transfer from the substrate, the label on the substrate must be on the phosphate group released from the enzyme. Ideally, the label can be isotopic and preferably radioactive in order to minimize the actual cost of the assay procedure. Hence, any isotopically labelled compound that is a substrate for protein phosphatases can be used to assess the activity of these enzymes in the process of the present invention. Preferably, the radiolabelled substrate should be a radiolabelled phosphopolypeptide (phosphoprotein or phosphopeptide) that is a substrate for protein phosphatase-1 and -2A. More preferably, the phosphopolypeptide should be phosphorylase. A phosphate group of this phosphopolypeptide could potentially be radiolabelled either at phosphorous, oxygen or one of the hydrogens. Alternatively, chemical strategies which measure the chemical loss of phosphate from the phosphopolypeptide substrate could also be used, such as mass spectrometry and the like.

Active fractions are referenced to a standard chromatogram where the assayed toxin is identified and quantitated by its characteristic retention time and protein phosphatase inhibition ratio, preferably its PP1:PP2A inhibition ratio.

A preferred embodiment of the process of the present invention will now be described in further detail.

1. Preparation of Standard Curves for the Inhibition of PP1 and PP2A by Okadaic Acid The biological activity of marine toxins, particularly okadaic acid, was assayed by the ability of these compounds to inhibit dephosphorylation of $^{32}$p-radiolabelled glycogen phosphorylase a (E. C. 2.4.1.1) by protein phosphatases (E. C. 3.1.3.16). In the preferred embodiment of the process of the present invention, the standard phosphorylase phosphatase assay described by Cohen et al. in (1988), Methods in Enzymology 159, 427–437, was used in okadaic acid inhibition studies.

Homogeneous PP-1 and -2A catalytic subunits were purified from rabbit skeletal muscle using the purification technique described by Cohen et al. in (1988), Methods in Enzymology, 159, 391–408. Radiolabelled phosphorylase a was prepared from phosphorylase b (Boehringer-Mannheim) by phosphorylation with $^{32}$P-γ-ATP (Amersham) and phosphorylase kinase (Sigma). Prior to use, phosphorylase kinase and phosphorylase b preparations were routinely pre-incubated with 25 mM NaF to inhibit endogenous phosphatase activity.

Thus, in order to confirm the ability of protein phosphatases to dephosphorylate phosphorylases, phosphorylase a (50 mg/ml) was diluted to 3 mg/ml (30 pmol/μl) in Tris HCl (50 mM, pH 7.0) containing ethylenediamine tetra-acetic acid (EDTA, 0.1 mM), bovine serum albumin (1 mg/ml), 2-mercaptoethanol (0.2% v/v) and caffeine (15 mM). An incubation comprising 10 μl protein phosphatase-1 or -2A (PP1/2A, 1 mU/ml in Tris HCl, pH 7.0) and 10 μl phosphatase inhibitor (in Tris HCl, pH 7.0) was carried out for 10 min at 30° C. An aliquot (10 μl) of phosphorylase a (30 pmol/μl, specific radioactivity $>0.6 \times 10^6$ dpm/nmol) was added to start the reaction, which was terminated after 10 min by adding 200 μl trichloroacetic acid (20% w/v, TCA). The suspension was vortexed, stood on ice for 1 min and centrifuged at 15,000 g for 2 min. An aliquot (200 μl) of supernatant was added to 1 ml scintillant and counted. One milliunit (mU) of protein phosphatase activity releases 1 nmol phosphatase from phosphorylase a per min. Thus, 10 μl of a 1 mU/ml solution of PP1/2A causes 33% dephosphorylation of phosphorylase a in 10 min in the standard assay, which is linear to this level of dephosphorylation.

Using a standard commercial preparation of okadaic acid, the $IC_{50}$ for PP1 and PP2A inhibition was 19 nM and 0.2 nM, respectively, in the standard phosphorylase a phosphatase assay as shown in FIG. 1. The $IC_{50}$'s correspond to okadaic acid detection limits of 432 pg (PP1) and 4.8 pg (PP2A) per μl when an unknown sample is added to the enzyme assay.

2. Fractionation of a Standard Okadaic Acid Mixture

Okadaic acid was from Moana Bioproducts Inc., Harding Ave, Suite 304, Honolulu, Hi. 9681, U.S.A. Dinophysistoxin-1 was isolated using the method described by Yasumoto et al. in (1985) Tetrahedron, Vol. 41, No. 6, pp. 1019-1025. Microcystin-LR was from Calbiochem.

An okadaic acid/dinophysistoxin-1 standard mixture was separated by reverse phase LC on a Vydac $C_{18}$ column (218TP54, Hesperia, Calif.) attached to a Hewlett-Packard HP1090M chromatograph. The standards, in methanol/0.1% trifluoroacetic acid (TFA) were applied to the column equilibrated in 0.1% TFA/H$_2$O and fractionated with a linear gradient of 0-100% acetonitrile/0.1% TFA in 40 min, at a flow rate of 1 ml/min. Typically, 1 ml fractions were collected and aliquots assayed against both PP1 and PP2A. Okadaic acid eluted reproducibly at 24 min (i.e. fraction 24) and dinophysistoxin-1 at 28 min.

Figure 2:
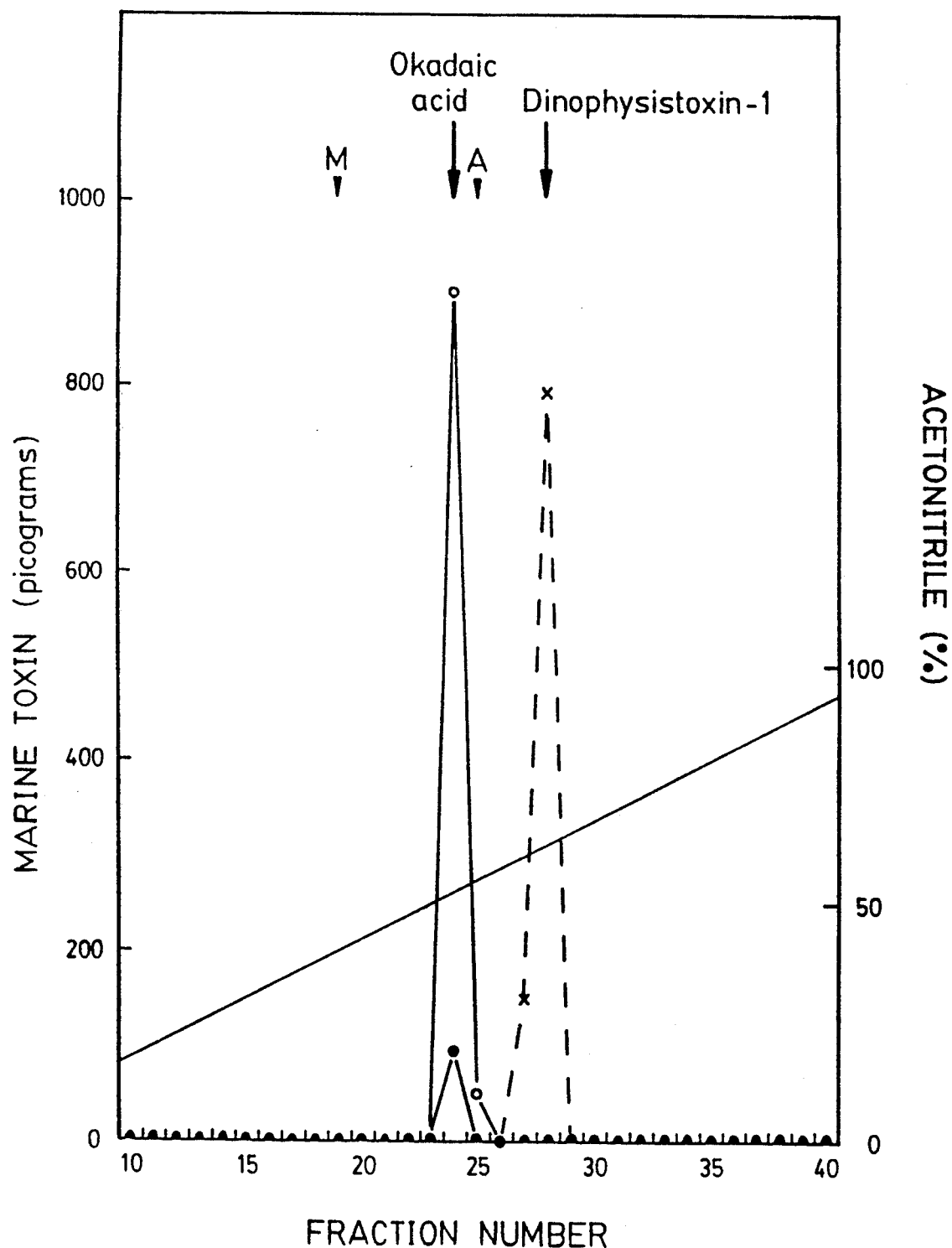
FIG. 2 represents the resolution of a standard mixture of okadaic acid and dinophysistoxin-1 by reverse phase LC.

FIG. 2 shows the resolution of the standard consisting of a mixture of 1 ng of each of okadaic acid (○—○) and dinophysistoxin-1 (x - - - x). The elution of a standard consisting of 100 pg of okadaic acid (●—●) is also shown. M and A correspond to the elution positions of the known protein phosphatase inhibitors, microcystin-LR and acanthifolicin, respectively. In order to obtain quantitative data, active fractions were diluted (when necessary) to give 40-55% inhibition in the standard assay, thus corresponding to the linear part of the dose-response relationship for phosphatase inhibition shown in FIG. 1.

Acanthifolicin (9, 10 epithio-okadaic acid) eluted at 25 min and was easily resolved from microcystin-LR, (a blue-green algae phosphatase inhibitor described by MacKintosh et al. in (1990), FEBS Lett. 264, 187-192), which eluted at 19 min.

3. Preparation of a Marine Extract

Mussel extracts were prepared by polytron homogenisation of fresh digestive tract or whole animal in 80% methanol/20% H$_2$O (0.3 g tissue/ml). Mussel extract aliquots were initially analyzed by their ability to inhibit PP1 and PP2A. When appropriate, methanolic mussel extracts (from 0.01-1.0 g tissue) were made 0.1% in TFA, fractionated by reverse phase LC using the standard protocol described below and aliquots quantitated for PP1/2A inhibition.

4. Measurement of the Amount of DSP Toxins Present in a Marine Extract

Experiments conducted in triplicate with control mussels (whole animal or digestive tract only) injected with or without 100 pg, 1 and 10 ng okadaic acid, then sonicated in 80% methanol/20% H$_2$O, established that the PP2A inhibition assay could be used as an initial screen to assess the maximum level of okadaic acid present in these samples. Recoveries of okadaic acid were reproducible and exceeded 85% in all instances.

Confirmatory identification of these toxins was obtained by inspection of relative PP1:PP2A inhibition ratios. Okadaic acid/dinophysistoxin-1 both inhibit PP2A 90(+10)-fold more strongly than PP1. Microcystin-LR can be distinguished from okadaic acid, since it inhibits PP1 and PP2A with a similar $IC_{50}$ (0.1 nM) under the standard assay conditions described previously.

Figure 3:
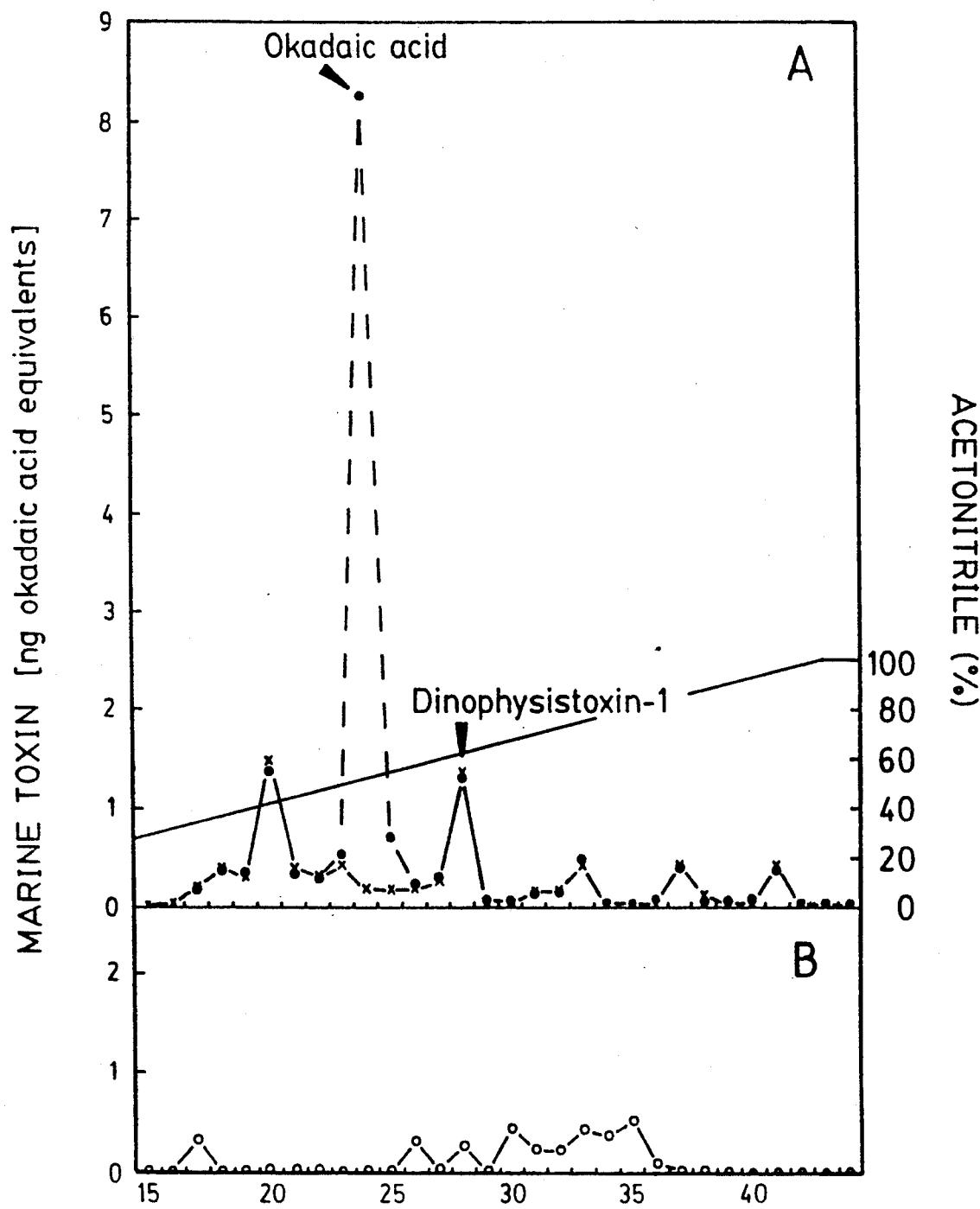
FIG. 3 represents LC-linked protein phosphatase-2A bioassay of suspected diarrhetic and control mussel extracts.

FIG. 3 shows the results of liquid chromatography-linked protein phosphatase-2A bioassay of suspected diarrhetic and control mussel extracts (Boxes A and B, respectively). The analysis corresponds to 1 g shellfish digestive tract. ●- - -● refers to mussel A with 10 ng okadaic acid added and x - - - x refers to mussel A with no okadaic acid added.

Inhibition assays of unfractionated mussel extract A revealed a maximum possible okadaic acid content of 10 ng per g digestive tract measured against PP2A.

All protein phosphatase inhibitors were conveniently quantitated against okadaic acid as a standard to give a uniform measurement of their relative biological activities. This method of analysis was obviated by the current lack of other commercially available DSP standards.

PP2A inhibitory activity in mussel extract A included inhibitors at 20 min (1.7 ng/g digestive tract) and 28 min (1.4 ng/g digestive tract).

The inhibitor at 28 min was identified as dinophysistoxin-1 on the basis of its elution position and characteristic PP1:PP2A inhibition ratio (1:85). This identification was supported by ion-spray mass spectrometry of 100 ng quantities of the fraction which revealed the presence of a characteristic dinophysistoxin-1 protonated molecular ion of mass 819. No okadaic acid was detected in the "unspiked" mussels either by phosphatase bioassay or mass spectrometry.

In order to assess the ability of LC-linked phosphatase bioassay to detect low ng quantities of okadaic acid in the presence of other phosphatase inhibitors, an equivalent quantity of mussel extract A (containing 1 g tissue) was spiked with 10 ng okadaic acid (as an internal standard). The sample was then refractionated and reassayed under identical conditions. Okadaic acid was recovered in excellent yield with 8.3 ng eluting at 24 min and 0.6 ng at 25 min (FIG. 3).

A further mussel extract was also analyzed from a different sampling location. This mussel had a relative PP1:PP2A inhibition ratio of 1:20. LC-phosphatase bioassay identified okadaic acid as the major phosphatase inhibitor present (6 ng/g digestive tract), eluting at 24 min. The presence of okadaic acid was confirmed by ion-spray mass spectrometry on 100 ng quantities, this revealed a protonated molecular ion of characteristic mass 805 in fraction 24.

The bioscreen developed in the context of the present invention was used to accurately quantitate okadaic acid/dinophysistoxin-1 in control, suspected diarrhetic and "okadaic acid spiked" diarrhetic mussels. The detection limit for okadaic acid/dinophysistoxin-1 was less than 10 pg when assayed against PP2A alone and less than 1 ng when assayed against PP1 and PP2A in combination. Dilution of PP2A in the standard assay to 0.03 mU/ml decreases the $IC_{50}$ for okadaic acid to 0.04 nM, in agreement with Cohen et al. in (1989), FEBS Letters, 250, 596-600. This lowers the detection limit to approximately 1 pg.

The methodology described was successfully applied to the sensitive analysis of microcystin-LR, a potent hepatotoxin and phosphatase inhibitor produced by marine cyanobacteria (FIG. 2), gramidicin-S, which has a PP1:PP2A inhibition ratio of 5:1 and elutes at 26 min in the standard LC protocol and may be applicable to tautomycin, a potent phosphatase inhibitor from Streptomyces sp..

The LC-linked protein phosphatase bioassay does not cross-react with paralytic or amnesic (domoic acid) shellfish toxins. Furthermore, PP1/PP2A are not inhibited by classical polyether antibiotics such as nigericin, monensin, maduramycin or salinomycin. Therefore the procedures described should provide a very useful addition to the increasing number of techniques available for analyzing DSP's. Since the enzymological components of the proposed bioscreen may soon become commercially available, the rapidity of the procedure could provide a large sample output for a single regional laboratory i.e. 90 assays per day per person (manually) or 700 assays per day (automated).

It should be noted that PP2A inhibition assays per se, whilst highly sensitive, provide only a maximum upper limit for the presence of okadaic acid and related DSP's. The presence of salts (such as NaF, which inhibits protein phosphatases) should always be borne in mind when analyzing crude marine extracts. These artefacts were removed by LC analysis since they eluted in the column breakthrough fractions. This explains why apparent total recovery of retained phosphatase inhibitory activity was approximately 40% after reverse phase LC of mussel extract A (FIG. 3).

The high sensitivity of the LC-phosphatase bioassay of the present invention means that the procedures described could be used to look for OA and DTX-1 in phytoplankton growing in the vicinity of shellfish. Therefore, this methodology is the first biological activity-based assay to have a pro-reactive (i.e. prior to shellfish uptake) capability for DSP detection. Its utility should therefore be of important commercial interest to worldwide shellfish aquaculture industries.

I claim:

1. A method for quantitatively assaying the presence in marine samples of diarrhetic shellfish poisoning (DSP) toxins having phosphatase inhibitory activity, said method comprising:
   preparing a marine extract;
   fractionating said marine extract to obtain a plurality of extract fractions, at least one of said fractions containing the toxin to be assayed;
   selecting the extract fraction containing the toxin to be assayed;
   incorporating at least one protein phosphatase inhibited by said toxin and a labelled physiological substrate acted upon by said phosphatase to said extract fraction; and
   quantitatively measuring the amount of toxin present in said extract fraction by means of said label and said substrate through the measurement of the ability of said fraction to inhibit catalysis of said labelled substrate by said protein phosphatase.

2. The method according to claim 1, wherein said labelled substrate is an isotopically labelled substrate.

3. The method according to claim 1, wherein said labelled substrate is a radiolabelled substrate.

4. The method according to claim 1, wherein said DSP toxin is okadaic acid.

5. The method according to claim 1, wherein said marine extract is fractionated by liquid chromatography.

6. The method according to claim 5, wherein said liquid chromatography is reverse phase liquid chromatography.

7. The method according to claim 1, wherein said marine extract is fractionated by capillary zone electrophoresis.

8. The method according to claim 3, wherein said radiolabelled substrate is a radiolabelled phosphopolypeptide selected from the group consisting of phosphoprotein and phosphopeptide.

9. The method according to claim 8, wherein said radiolabelled phosphoprotein is radiolabelled phosphorylase.

10. The method according to claim 9, wherein said phosphorylase is labelled with $^{32}P\text{-}\gamma\text{-ATP}$.

11. The method according to claim 1, wherein said protein phosphatase is phosphatase-1 and/or phosphatase-2A.

12. The method according to claim 1, wherein said marine extract is prepared by homogenizing a marine sample in a solvent allowing solubilization of marine toxins present in said sample.

13. The method according to claim 12, wherein said solvent is methanol.

14. The method according to claim 1, wherein said extract fraction containing the toxin to be assayed is selected based on a quantitative standard curve for the toxin to be assayed, when assayed against at least one protein phosphatase.

15. The method according to claim 1, wherein the quantity of toxin present in said extract fraction is measured by referencing said fraction to a standard chromatogram where said toxin is identified and quantitated by its characteristic retention time and PP1:PP2A inhibition ratio.

16. The method according to claim 1, wherein said DSP toxin is dinophysistoxin-1.

17. The method according to claim 1, wherein said protein phosphatase exhibited by said toxin is a serine/threonin protein phosphatase.

* * * * *